United States Patent [19]

Kollman

[11] Patent Number: 4,508,559

[45] Date of Patent: Apr. 2, 1985

[54] HERBICIDAL COMPOSITIONS

[75] Inventor: Garald E. Kollman, Libertyville, Ill.

[73] Assignee: Rohm and Haas Company, Philadelphia, Pa.

[21] Appl. No.: 505,119

[22] Filed: Jun. 20, 1983

Related U.S. Application Data

[63] Continuation of Ser. No. 99,769, Dec. 3, 1979, abandoned, which is a continuation of Ser. No. 732,621, Oct. 15, 1976, abandoned.

[51] Int. Cl.$^3$ ............................................. A01N 37/48
[52] U.S. Cl. ............................................. 71/83; 71/65; 71/70; 71/86; 71/113; 71/115; 71/124; 71/97
[58] Field of Search ................... 71/83, 115, 113, 86, 71/124, 70, 65

[56] References Cited

U.S. PATENT DOCUMENTS

| | | | |
|---|---|---|---|
| 2,629,655 | 2/1953 | Stark, Jr. | 71/65 |
| 2,869,996 | 1/1959 | Vierling | 71/29 |
| 3,036,908 | 5/1962 | Gunther | 71/117 |
| 3,457,062 | 7/1969 | Young | 71/70 |
| 3,558,300 | 1/1971 | Wagner | 71/34 |
| 3,798,276 | 3/1974 | Bayer et al. | 71/108 |
| 3,928,416 | 12/1975 | Bayer et al. | 71/108 |
| 4,038,064 | 7/1977 | Clapp et al. | 71/29 |

OTHER PUBLICATIONS

Suwunnamek et al., "Control of Cyperus Rotundres, etc.; " (1975) Weed. Res. 15, pp. 13–19 (1975).
Turner et al., "Further Studies with Additives, etc.; " (1975) Pestic. Sci. 6, pp. 1–10 (1975).
Wilson et al., "Ammonium Sulfate etc.; " (1975) Weed Sci. 23, pp. 289–296 (1975).
Babiker et al., "Pentration of Pracken Fronds, etc.;" (1974) Weed Res. 15, pp. 123–127 (1975).

*Primary Examiner*—Richard L. Raymond
*Attorney, Agent, or Firm*—Polly E. Ramstad

[57] ABSTRACT

Herbicidal compositions which comprise 2-chloro-α,α,α-trifluoro-p-tolyl-3-carboxy-4-nitrophenyl ether, or agronomically-acceptable salts thereof, and at least one water-soluble salt of an inorganic or organic acid have enhanced herbicidal activity when compared to similar compositions lacking the water-soluble salt.

10 Claims, No Drawings

HERBICIDAL COMPOSITIONS

CROSS RELATED PATENT APPLICATIONS

This is a continuation of application Ser. No. 99,769 filed Dec. 3, 1979, abandoned, which is a continuation of application Ser. No. 732,621 filed Oct. 15, 1976, now abandoned.

This invention relates to methods for enhancing the herbicidal activity of certain diphenyl ether herbicides, and to herbicidal compositions having enhanced activity.

Various organic and inorganic salts have been used in the past to increase the activity of herbicides in specific applications. However, such salts have also been found to be totally ineffective in enhancing the activity of various other herbicides, including, paraquat for example. Furthermore, water-soluble salts have not been used heretofore with diphenyl ether herbicides to improve their activity. It has now been found that water-soluble inorganic and organic salts will unexpectedly enhance the herbicidal activity of certain diphenyl ether herbicides, while having no such effect when used in combination with other closely-related diphenyl ether herbicides.

According to the invention herbicidal compositions which comprise (a) a diphenyl ether herbicide selected from the group consisting of 2-chloro-$\alpha,\alpha,\alpha$-trifluoro-p-tolyl-3-carboxy-4-nitrophenyl ether and agronomically-acceptable salts thereof, and (b) at least one water soluble salt of an inorganic or organic acid have herbicidal activity which is significantly greater than similar compositions which lack the salt. Thus, the compositions of the invention permit the use of a smaller amount of the diphenyl ether herbicide to achieve the same degree of herbicidal efficacy. Generally, the composition will contain a weight ratio of herbicide to salt of about 10:1 to about 1:500, and preferably about 3:1 to about 1:100.

In preparing the compositions of the invention, any water-soluble salt of an inorganic or organic acid (other than a salt of the diphenyl ethers named above) can be used. By "water-soluble" is meant solubility of the salt in water at 20° C. of at least about 10 grams/liter. Among the preferred salts used in the compositions of the invention are the metal salts, especially the alkali metal salts, such as sodium and potassium salts, the alkaline earth metal salts, such as calcium and magnesium salts, and ammonium salts, including alkyl-, aryl-, and aralkyl-substituted ammonium salts, of acetic acid, benzoic acid, oxalic acid, phosphoric acid, sulfuric acid, nitric acid, perchloric acid, carbonic acid, hydrobromic acid, hydrochloric acid, and the like. Heavy metal salts, such as copper salts, are also useful. Typical salts include ammonium phosphate, ammonium monohydrogen phosphate, ammonium dihydrogen phosphate, ammonium sulfate, ammonium chloride, potassium sulfate, potassium phosphate, potassium hydrogen phosphate, potassium dihydrogen phosphate, potassium nitrate, potassium chloride sodium nitrate, sodium phosphate, sodium monohydrogen phosphate, sodium dihydrogen phosphate, sodium chloride, sodium sulfate, sodium acetate, and the like. The most preferred salts are the ammonium, sodium, and potassium sulfates, nitrates, phosphates, hydrogen phosphates, and dihydrogen phosphates. If the salt is, for example, a phosphate, the salt can be present in the composition as a buffer with the pH adjusted to about pH 7.

The compositions of the invention are typically formulated as concentrated aqueous solutions, as soluble formulated powders containing both the herbicide and the salt, or as separate concentrated solutions or soluble formulated powders, one containing the herbicide and the other the water-soluble salt. The formulation can then be diluted to appropriate use concentrations with water. In the concentrated solutions, the salt will generally comprise about 5 to about 50 percent by weight and the herbicide about 5 to about 50 percent by weight of the composition. In the soluble formulated powders, the weight ratio of herbicide to water-soluble salt will generally be about 10:1 to about 1:500. The concentrated solutions and the formulated powders are diluted with water to give a carrier volume of generally about 5 to about 50 gallons/acre at the desired rate of application of the herbicide.

The herbicidal compositions of the invention are useful as preemergence herbicides and, more preferably, as postemergence herbicides. Among the crops on which the compositions of the invention can be advantageously employed are, for example, soybeans, peanuts, peas, greenbeans, dry beans, lima beans, rice, corn, wheat, barley and the like. The compositions can be applied in any amount which will give the required control of weeds, and are generally applied at a rate of about 0.1 to about 12 pounds of the diphenyl ether herbicide per acre.

The compositions of the invention are generally applied to the area of treatment as herbicidal sprays. Application can be carried out by appropriate conventional techniques, such as high gallonage hydraulic sprays, low gallonage sprays, airblast spray, aerial sprays, and the like. The dilution and rate of application can be varied and will usually depend upon such factors as the type of equipment employed, the method of application, the area to be treated, and the type and stage of development of the weeds.

The diphenyl ether herbicides which are the active ingredients in the compositions are known herbicides, and are described in U.S. Pat. Nos. 3,798,276, of Bayer et al., granted Mar. 19, 1974, 3,928,416 of Bayer et al., granted Dec. 23, 1975, and U.S. Ser. No. 617,560, of Bayer et al., filed Sept. 29, 1975. When the diphenyl ether herbicide is used in the form of its salt, the sodium, potassium, or ammonium salt is preferred.

The following examples will further illustrate this invention, but are not intended to limit it in any way. All temperatures are in degrees Centigrade and parts and percentages by weight unless otherwise indicated.

EXAMPLE 1

This example shows the enhanced postemergence herbicidal activity of compositions comprising the sodium salt of 2-chloro-$\alpha,\alpha,\alpha$-trifluoro-p-tolyl-3-carboxy-4-nitrophenyl ether as the active ingredient.

Formulations are prepared as aqueous solutions of the diphenyl ether herbicide to which various concentrations of several water-soluble salts are added. The herbicidal activity of these compositions is then compared to similar formulations containing no additional water-soluble salt.

The following text procedure is employed. Seeds of selected crops and weeds are planted in soil in pots. The seeds are allowed to germinate, and after two weeks the pots are sprayed with the test formulations, using a belt spray at a volume of 50 gallons per acre. About two weeks after the test formulation is applied, the state of growth of the plants is observed and the phytotoxic effect of each formulation is evaluated for percent control in terms of the percent of the plants which are killed by the test formulation. The following plant species were included in the tests:

- cocklebur (*Xanthium pensylvanicum*)
- morningglory (Ipomoea spp.)
- velvetleaf (*Abutilon theophrasti*)
- wild oats (*Avena fatua*)
- soybean (*Glycine max*)
- tomato (*Lycopersicon esculentum*)
- marigold (Tagetes spp.)

Tables I to III summarize typical results of these tests.

TABLE I

| Herbicide Rate | Water | NH₄H₂PO₄¹ 0.3 N | 0.03 N | NaNO₃ 0.3 N | 0.03 N | Sodium Acetate 0.3 N | 0.03 N | Potassium Phosphate² 0.3 N | 0.03 N | (NH₄)₂SO₄ 0.3 N | 0.03 N |
|---|---|---|---|---|---|---|---|---|---|---|---|
| Cocklebur | | | | | | | | | | | |
| 0 | 0 | 0 | 0 | 0 | 0 | 0 | 0 | 0 | 0 | 0 | 0 |
| ⅛ | 20 | 20 | 20 | 30 | 20 | 20 | 20 | 20 | 20 | 20 | 0 |
| ¼ | 30 | 40 | 40 | 50 | 40 | 30 | 30 | 50 | 0 | 0 | 0 |
| ½ | 50 | 60 | 60 | 70 | 60 | 70 | 40 | 50 | 50 | 50 | 0 |
| Morningglory | | | | | | | | | | | |
| 0 | 0 | 0 | 0 | 0 | 0 | 0 | 0 | 0 | 0 | 0 | 0 |
| ⅛ | 20 | 50 | 90 | 20 | 30 | 30 | 30 | 20 | 10 | 20 | 0 |
| ¼ | 20 | 100 | 90 | 50 | 30 | 50 | 50 | 50 | 30 | 100 | 0 |
| ½ | 30 | 98 | 90 | 40 | 30 | 75 | 60 | 90 | 30 | 95 | 0 |
| Velvetleaf | | | | | | | | | | | |
| 0 | 0 | 0 | 0 | 0 | 0 | 0 | 0 | 0 | 0 | 0 | 0 |
| ⅛ | 10 | 95 | 85 | 40 | 20 | 50 | 50 | 90 | 30 | 30 | 0 |
| ¼ | 40 | 99 | 80 | 90 | 60 | 99 | 70 | 95 | 95 | 100 | 0 |
| ½ | 70 | 100 | 100 | 99 | 90 | 99 | 85 | 100 | 100 | 100 | 0 |
| Wild Oats | | | | | | | | | | | |
| 0 | 0 | 0 | 0 | 0 | 0 | 0 | 0 | 0 | 0 | 0 | 0 |
| ⅛ | 0 | 20 | 30 | 70 | 0 | 20 | 20 | 0 | 20 | 5 | 0 |
| ¼ | 30 | 50 | 70 | 85 | 40 | 50 | 30 | 75 | 30 | 50 | 0 |
| ½ | 70 | 80 | 80 | 90 | 60 | 80 | 85 | 85 | 85 | 90 | 0 |
| Total All Weeds | 390 | 816 | 835 | 734 | 480 | 673 | 570 | 745 | 590 | 649 | 0 |
| Soybeans | | | | | | | | | | | |
| 0 | 0 | 0 | 0 | 0 | 0 | 0 | 0 | 0 | 0 | 0 | 0 |
| ⅛ | 0 | 10 | 10 | 10 | 0 | 10 | 10 | 10 | 0 | 5 | 0 |
| ¼ | 0 | 20 | 15 | 15 | 10 | 15 | 15 | 20 | 20 | 20 | 0 |
| ½ | 10 | 30 | 30 | 25 | 10 | 20 | 15 | 20 | 20 | 25 | 0 |
| Total | 10 | 60 | 55 | 50 | 20 | 45 | 40 | 50 | 50 | 50 | 0 |

¹pH not adjusted
²buffer at pH of 7.0

TABLE II

| Herbicide Rate | Water | (NH₄)₂SO₄ 0.3 N | 0.03 N | Potassium Phosphate Buffer 0.3 N | 0.03 N |
|---|---|---|---|---|---|
| Cocklebur 0 | 0 | 0 | 0 | 0 | 0 |
| ⅛ | 30 | 40 | 40 | 40 | 40 |
| ¼ | 30 | 80 | 40 | 40 | 50 |
| ½ | 60 | 99 | 90 | 70 | 60 |
| Morningglory 0 | 0 | 10 | 10 | 0 | 10 |
| ⅛ | 20 | 100 | 90 | 80 | 20 |
| ¼ | 20 | 90 | 90 | 95 | 50 |
| ½ | 50 | 99 | 85 | 90 | 70 |
| Velvetleaf 0 | 0 | 0 | 0 | 0 | 0 |
| ⅛ | 20 | 10 | 5 | 0 | 0 |
| ¼ | 20 | 0 | 5 | 0 | 0 |
| ½ | 50 | 10 | 10 | 0 | 0 |
| Wild Oats 0 | 0 | 0 | 0 | 0 | 0 |
| ⅛ | 20 | 0 | 0 | 0 | 0 |
| ¼ | 20 | 0 | 5 | 0 | 0 |
| ½ | 50 | 5 | 5 | 0 | 0 |
| Total | 400 | 502 | 450 | 495 | 300 |
| Soybean 0 | 0 | 0 | 0 | 0 | 0 |
| ⅛ | 0 | 0 | 0 | 0 | 0 |
| ¼ | 0 | 5 | 0 | 5 | 5 |
| ½ | 20 | 5 | 5 | 5 | 5 |
| Total | 40 | 10 | 0 | 10 | 10 |

TABLE III

| Herbicide Rate | % Control⁽¹⁾ Water | Potassium Phosphate buffer 0.3 N | 0.03 N | 0.003 N | Sodium phosphate buffer | Sodium Chloride | Sodium sulfate |
|---|---|---|---|---|---|---|---|
| 0 | 0 | 0 | 0 | 0 | 0 | 0 | 0 |
| ¼ | 56 | 48 | 4 | 0 | 0 | 0 | 0 |
| ½ | 83 | 100 | 90 | 85 | 0 | 4 | 0 |
| Total | 139 | 198 | 94 | 85 | 0 | 4 | 0 |

⁽¹⁾Average of cocklebur, velvetleaf, morningglory, marigold and tomato

EXAMPLE 2

Following the procedure of Example 1, aqueous compositions comprising the sodium salt of 2-chloro-α,α,α-trifluoro-p-tolyl-3-(1-carboxyethoxy)-4-nitrophenyl ether (Compound B) and 2-chloro-α,α,α-trifluorop-tolyl-3-carboxy-4-nitrophenyl ether, as the free acid, (Compound C) both with and without ammonium sulfate (0.3N) were compared for herbicidal activity against cocklebur, morningglory, velvetleaf, wild oats, and soybean. Table IV summarizes typical results of these tests.

TABLE IV

| Compound | Rate (lb/A) | Salt | Cocklebur | morningglory | velvetleaf | wild oats | avg.-all weeds | soybean |
|---|---|---|---|---|---|---|---|---|
| B | 1/32 | yes | 100 | 95 | 100 | 20 | | 20 |
|   |      | no  | 40  | 30  | 70  | 20 | | 30 |
|   | 1/16 | yes | 100 | 100 | 100 | 30 | | 30 |
|   |      | no  | 90  | 60  | 85  | 20 | | 50 |
|   | ⅛    | yes | 90  | 100 | 100 | 40 | | 60 |
|   |      | no  | 100 | 80  | 70  | 30 | | 40 |
|   | ¼    | yes | 100 | 100 | 100 | 50 | | 95 |
|   |      | no  | 99  | 100 | 97  | 50 | | 40 |
|   |      | yes |     |     |     |    | 83 |    |
|   |      | no  |     |     |     |    | 65 |    |
| C | ⅛    | yes | 60  | 99  | 100 | 30 | | 20 |
|   |      | no  | 50  | 60  | 40  | 10 | | 20 |
|   | ¼    | yes | 70  | 100 | 100 | 60 | | 30 |
|   |      | no  | 60  | 95  | 99  | 40 | | 20 |
|   | ½    | yes | 100 | 100 | 100 | 70 | | 30 |
|   |      | no  | 95  | 99  | 100 | 60 | | 20 |
|   |      | yes |     |     |     |    | 82 |    |
|   |      | no  |     |     |     |    | 67 |    |

The above data demonstrates that formulation of Compound B and Compound C with a water-soluble salt enhances their herbicidal activity, especially against broadleaf weeds.

It is to be understood that changes and variations can be made without departing from the spirit and scope of this invention as defined by the appended claims.

I claim:

1. A herbicidal composition comprising (a) a herbicide selected from the group consisting of 2-chloro-alpha, alpha, alpha-trifluoro-p-tolyl-3-carboxy-4-nitrophenyl ether and agronomically-acceptable salts thereof and (b) at least one water-soluble alkali metal, alkaline earth metal or ammonium salt of an acid selected from the group consisting of acetic acid, benzoic acid, oxalic acid, phosphoric acid, sulfuric acid, nitric acid, perchloric acid, carbonic acid, hydrobromic acid, and hydrochloric acid wherein the weight ratio of the herbicide to the water-soluble salt is about 3:1 to about 1:100.

2. A herbicidal composition comprising (a) a herbicide selected from the group consisting of 2-chloro-alpha,alpha,alpha-trifluoro-p-tolyl-3-carboxy-4-nitrophenyl ether and agronomically-acceptable salts thereof and (b) at least one water-soluble sodium, potassium, magnesium, calcium or ammonium salt of phosphoric acid, sulfuric acid, nitric acid, acetic acid or hydrochloric acid wherein the weight ratio of the herbicide to the water-soluble salt is about 3:1 to about 1:100.

3. The composition of claim 2 wherein the herbicide is 2-chloro-alpha,alpha,alpha-trifluoro-p-tolyl-3-carboxy-4-nitrophenyl ether or its sodium, potassium or ammonium salt.

4. A herbicidal composition comprising (a) a herbicide selected from the group consisting of 2-chloro-alpha,alpha,alpha-trifluoro-p-tolyl-3-carboxy-4-nitrophenylether and agronomically acceptable alkali metal salts thereof and (b) at least one water-soluble sodium, potassium or ammonium salt of phosphoric acid, sulfuric acid, nitric acid or hydrochloric acid wherein the weight ratio of the herbicide to the water-soluble salt is about 3:1 to about 1:85.

5. The composition of claim 4 wherein the water-soluble salt of an acid is ammonium phosphate, ammonium monohydrogen phosphate, ammonium dihydrogen phosphate, sodium phosphate, sodium monohydrogen phosphate, sodium dihydrogen phosphate, potassium phosphate, potassium monohydrogen phosphate, potassium dihydrogen phosphate, ammonium nitrate, sodium nitrate, potassium nitrate, ammonium sulfate, sodium sulfate, or potassium sulfate wherein the weight ratio of the herbicide to the water-soluble salt is from about 1:1 to 1:32.

6. The composition of claim 5 wherein the water-soluble salt is ammonium nitrate, sodium sulfate, ammonium sulfate, ammonium phosphate, ammonium monohydrogen phosphate, ammonium dihydrogen phosphate, potassium phosphate, potassium monohydrogen phosphate, potassium dihydrogen phosphate, sodium phosphate, sodium monohydrogen phosphate, and sodium dihydrogen phosphate.

7. The composition of claim 6 wherein the water-soluble salt is potassium phosphate, potassium monohydrogen phosphate, potassium dihydrogen phosphate, ammonium phosphate, ammonium monohydrogen phosphate or ammonium dihydrogen phosphate.

8. The composition of claim 7 wherein the salt is a potassium phosphate buffer or ammonium monohydrogen phosphate.

9. The composition of claim 4 where the composition is applied at a rate of from about 0.1 to about 0.5 pounds of herbicide per acre and from about 0.1 to about 10 pounds of salt per acre.

10. In a process of combatting weeds in an agronomic crop locus, the improvement of spraying said weeds with an aqueous composition containing a combination of (a) 2-chloro-alpha,alpha,alpha-trifluoro-p-tolyl-3-carboxy-4-nitrophenyl ether, or an agronomically acceptable salt thereof, and (b) at least one water-soluble alkali metal, alkaline earth metal or ammonium salt of phosphoric acid, sulfuric acid, nitric acid, acetic acid or hydrochloric acid wherein the weight ratio of the herbicide to the water-soluble salt is about 3:1 to about 1:100, said aqueous composition being sprayed at about 5 to about 50 gallons of water per acre, the composition being applied at a rate of about 0.1 to about 12 pounds of the diphenyl ether herbicide per acre, the rate being sufficient to control the growth of the weeds.

* * * * *

UNITED STATES PATENT AND TRADEMARK OFFICE
CERTIFICATE OF CORRECTION

PATENT NO. : 4,508,559

DATED : April 2, 1985

INVENTOR(S) : Gerald E. Kollman

It is certified that error appears in the above-identified patent and that said Letters Patent is hereby corrected as shown below:

On the title page

Inventor: change "Garald" to -- Gerald --.

Column 2, line 63: change "text" to -- test --.

Signed and Sealed this

Fifth Day of November 1985

[SEAL]

Attest:

Attesting Officer

DONALD J. QUIGG

Commissioner of Patents and Trademarks